(12) United States Patent
Valente et al.

(10) Patent No.: US 8,914,117 B2
(45) Date of Patent: Dec. 16, 2014

(54) APPARATUS FOR PERFORMING DEEP BRAIN STIMULATION WITH A HIGH FREQUENCY ELECTRIC FIELD

(75) Inventors: Virgilio Valente, London (GB); Andreas Demosthenous, London (GB); Richard Bayford, Hendon (GB)

(73) Assignee: UCL Business PLC, London (GB)

( * ) Notice: Subject to any disclaimer, the term of this patent is extended or adjusted under 35 U.S.C. 154(b) by 313 days.

(21) Appl. No.: 13/130,279

(22) PCT Filed: Nov. 20, 2009

(86) PCT No.: PCT/GB2009/002721
§ 371 (c)(1),
(2), (4) Date: Sep. 6, 2011

(87) PCT Pub. No.: WO2010/058178
PCT Pub. Date: May 27, 2010

(65) Prior Publication Data
US 2011/0313236 A1    Dec. 22, 2011

(30) Foreign Application Priority Data
Nov. 21, 2008   (GB) .................................. 0821325.8

(51) Int. Cl.
*A61N 1/36*    (2006.01)
*A61N 1/05*    (2006.01)

(52) U.S. Cl.
CPC ........... *A61N 1/36082* (2013.01); *A61N 1/0534* (2013.01)
USPC .......................................................... 607/45

(58) Field of Classification Search
None
See application file for complete search history.

(56) References Cited

U.S. PATENT DOCUMENTS

| | | | |
|---|---|---|---|
| 5,713,922 A * | 2/1998 | King | 607/2 |
| 5,800,465 A * | 9/1998 | Thompson et al. | 607/9 |
| 5,895,416 A * | 4/1999 | Barreras et al. | 607/62 |
| 6,353,762 B1 * | 3/2002 | Baudino et al. | 607/45 |
| 6,505,078 B1 | 1/2003 | King | |
| 7,363,079 B1 * | 4/2008 | Thacker et al. | 607/27 |
| 2002/0099412 A1 * | 7/2002 | Fischell et al. | 607/3 |
| 2002/0183817 A1 * | 12/2002 | Van Venrooij et al. | 607/116 |
| 2002/0188330 A1 * | 12/2002 | Gielen et al. | 607/45 |
| 2006/0253182 A1 * | 11/2006 | King | 607/117 |
| 2007/0142874 A1 * | 6/2007 | John | 607/45 |

(Continued)

FOREIGN PATENT DOCUMENTS

| | | |
|---|---|---|
| WO | 0245795 A2 | 6/2002 |
| WO | 2008072125 A1 | 6/2008 |
| WO | 2008157182 A1 | 12/2008 |

OTHER PUBLICATIONS

Valente, Virgilio et al., "Modeling the Behavior of Phased Arrays in Brain Tissue: Application to Deep Brain Stimulation", COMSOL Conference, 2009.

(Continued)

*Primary Examiner* — Kennedy Schaetzle
(74) *Attorney, Agent, or Firm* — Park, Vaughan, Fleming & Dowler LLP

(57) ABSTRACT

One embodiment of the invention provides a method and apparatus for performing deep brain stimulation with an electromagnetic field. The includes an electrode assembly having multiple electrodes and a phased array system for driving the electrodes to generate the electromagnetic field. By controlling delays within the phased array system, the generated electromagnetic field can be steered to a desired region of the brain.

13 Claims, 8 Drawing Sheets

(56) References Cited

U.S. PATENT DOCUMENTS

| | | | |
|---|---|---|---|
| 2009/0112273 A1* | 4/2009 | Wingeier et al. | 607/3 |
| 2009/0118787 A1* | 5/2009 | Moffitt et al. | 607/45 |
| 2010/0125312 A1* | 5/2010 | Stevenson et al. | 607/45 |
| 2011/0106214 A1* | 5/2011 | Carbunaru et al. | 607/60 |

OTHER PUBLICATIONS

Valente, Virgilio et al., "Poster Presentation: Modeling the Behavior of Phased Arrays in Brain Tissue: Application to Deep Brain Stimulation", COMSOL Conference, 2009.

Anonymous: "Final Program: Multiphysics Modeling and Stimulation", COMSOL Conference, 2009.

\* cited by examiner

APPARATUS FOR PERFORMING DEEP BRAIN STIMULATION WITH A HIGH FREQUENCY ELECTRIC FIELD

TECHNICAL FIELD

This invention relates to performing deep brain stimulation with an electromagnetic field for the investigation and treatment of various neurological disorders, and in particular to controlling and directing the stimulating electromagnetic field within the brain.

BACKGROUND OF THE INVENTION

Deep brain stimulation (DBS) is a clinical tool in which an electric field is used to treat various neurological disorders, including Parkinson's disease, dystonia, epilepsy, obsessive-compulsive disorder, chronic pain and incontinence. Conventional drug and surgical treatments for such conditions suffer from various problems, including lack of efficacy, side effects, and the potential to cause irreversible damage to the brain. Benabid and colleagues assessed the benefits of applying high-frequency electric field stimulation to the ventral intermediate nucleus—see "Long-term suppression of tremor by chronic stimulation of the ventral intermediate thalamic nucleus", Lancet, vol. 337, no. 8738, pp. 403-406, February 1991. Substantial long-term improvements were reported on several cases of patients affected by Parkinson's disease, essential tremor and other movement disorders. The therapeutic effectiveness of DBS has lead to its adoption as standard treatment for movement disorders.

Although DBS is generally considered in terms of the electric field, the applied field usually represents an electromagnetic field with both electric and magnetic components. Accordingly references herein to the electric field should be understood as appropriate to encompass also the accompanying magnetic field. However, the magnetic component is generally negligible at conventional DBS frequencies (about 100-200 Hz), and stimulation is provided primarily by the static (DC) component of the electric field.

FIG. 1 illustrates in schematic form the use of a DBS system. The system includes an electrode assembly which has a long, thin shape (like a needle) for easier insertion into the brain. The main shaft of the electrode assembly is covered by insulator, and includes or comprises an insulated wire. A number of electrodes, made, for example, of platinum iridium, are located at the distal end of the shaft for insertion deep into the brain. The proximal end of the electrode assembly is connected to an extension lead, which links the electrode assembly to a pulse generator.

The pulse generator is normally implanted into the subject and placed subcutaneously below the clavicle or, in some cases, the abdomen (and hence is referred to as an implanted pulse generator or IPG). The IPG is a battery-powered neural stimulator which sends electrical pulses to the brain via the electrode assembly. The IPG is connected to the electrode assembly by an extension lead, an insulated wire that normally runs from the head, down the side of the neck, behind the ear to the IPG.

Typical clinical settings used by the IPG are a pulse amplitude of approximately 2.5-3.5V, a pulse width of approximately 60-120 µs, a pulse repetition rate of approximately 130-185 pulses per second, and the use of unipolar or bipolar pulses. Note that a higher pulse rate is generally ineffective, since the neurons must have time to reset between pulses for a subsequent pulse to be effective.

In practice a DBS procedure involves the precise location of an electrode assembly comprising one or more electrodes into a particular region of the brain, depending on the condition being treated. For example, the subthalamic nucleus (STN) (part of the basal ganglia) is a common target site for addressing Parkinson's disease. Once the electrodes and associated leads have been inserted into the brain, the leads are immobilised at the entry point in the skull. Typically there is a two week delay to allow the trauma of the operation to subside before the electrodes are activated. At this point one or more of the electrodes are used to deliver electrical stimulation into the brain.

There are two main reasons for providing multiple electrodes in the electrode assembly. The first reason is to monitor impedance between electrodes as the electrode assembly is being inserted into the brain. A change in impedance indicates that the assembly may have penetrated a different region of the brain (e.g. the ventricle). This information can then be used to help guide placement of the assembly within the head. The second reason is to give additional flexibility when activating the electric field. Thus for any given position of the electrode assembly in the brain, the clinician may select a particular electrode (or, most commonly, pair of electrodes) to activate that provides the best patient response.

It has been found that the effectiveness of the treatment is highly dependent on the placement of the electrodes, the volume of brain tissue activated (VTA) by the field from the electrodes, and the type of neural tissue influenced. However, after the electrodes have been implanted in the brain, physicians are left with limited control over the effects of stimulation and, in particular, over the shape and direction of the electric field propagating around the electrode. This propagation is mainly a function of the physiological properties of the brain target area, and only marginally of the stimulator setting.

Depending on the particular circumstances, DBS may activate (excite) some neurons into firing, while it may also inhibit other neurons (i.e. prevent them from firing when they otherwise would). In general the electric field will only effect a given neuron if the field is above a certain strength, otherwise the neuron will not be activated (or inhibited). Accordingly, the VTA corresponds to the region where the electric field generated by the DBS system is strong enough to impact neural activity.

Improving control of the VTA is important for enhancing the effectiveness of DBS, as well as reduced unwanted side effects caused by areas of the brain that are unintentionally stimulated by the electrodes. WO 2008/038208 discloses one tissue stimulation apparatus having a two dimensional array of electrodes that support a time-varying electrical stimulation scheme. U.S. Pat. No. 2008/020823 also discloses a two-dimensional configuration of electrodes for DBS. Although both of these devices may provide improved positioning of the electric field, they require a large number of electrodes in a relatively complex configuration, and this in itself impacts (shunts) the electric field.

Although DBS is now a widely accepted technology, it is highly invasive, and hence there is very limited scope for performing in-vivo measurements. Accordingly, the past decades have seen a significant effort dedicated to the development of computerized models to determine the electric field and VTA by stimulation (this being closely related to the clinical benefit of DBS and its potential side effects).

Given the difficulty of measuring the VTA during therapeutic stimulations, researchers have attempted to characterize quantitatively the VTA by adopting of two or three-dimensional models of the DBS electrodes and the anatomical structure of the stimulation target. This work has highlighted the inability of current DBS systems to control the distribution of the potential field and the shape and direction of the electric field propagating around the electrodes. It is therefore desirable to develop a DBS system which allows improved control of the direction, shape and intensity of the electric field propagating from the electrodes into the brain, both for achieving improved clinical outcomes, and also for helping to investigate, at a more fundamental level, the operation of DBS within the brain.

SUMMARY OF THE INVENTION

One embodiment of the invention provides apparatus for performing deep brain stimulation with an electric (electromagnetic) field. The apparatus includes an electrode assembly having multiple electrodes and a phased array system for driving the electrodes to generate the electromagnetic field.

The used of a phased array system for driving the electrodes helps to provide better control over the electric field produced by the apparatus. This can be used to improve understanding of DBS mechanisms, for example by seeing how changes in the electromagnetic field affect a subject, and this in turn will help with the optimization of stimulation parameters. Improved control of the electric field can also help with other aspect of DBS systems, such as electrode design and battery lifetime. For example, being able to direct or concentrate the electromagnetic field to a specific desired location may reduce the overall size of field that the electrodes are required to produce.

In one embodiment, the multiple electrodes comprise a linear array of electrodes. This provides a relatively straightforward mechanism for controlling the direction of the electromagnetic field. However, in other embodiments, the electrodes may have any desired arrangement in three-dimensional space, including regular or irregular spacing, a one-dimension or two-dimensional layout (which may then be curved into a higher dimension), and so on.

In some embodiments, the multiple electrodes comprise 8 or more electrodes, for example, potentially 16 or more electrodes. In general, increasing the number of electrodes also increases the accuracy of steering the electromagnetic field, and hence may lead to a greater number of electrodes than common for existing DBS apparatus. Furthermore, all the electrodes may be active together as part of operating the DBS apparatus as a phased array system. In contrast, many existing systems will only activate perhaps two electrodes during normal operations.

In one embodiment, the phased array system generates a high frequency sinusoidal signal for supply to the multiple electrodes. The phase of the signal is staggered between different electrodes to steer the electric field. The sinusoidal signal has a frequency above about 1 GHz and a corresponding wavelength in the brain comparable with the volume of tissue to be activated. This signal frequency is much higher than for existing DBS systems. A periodic on-off duty cycle may be imposed onto the sinusoidal signal, for example having a frequency in the range 100-200 Hz, where the "on" portion of the duty cycle has a period in the range 1-100 μs.

In another embodiment, the phased array system generates a Gaussian pulsed signal (with no dc component). The timing of the pulse signal is staggered between the different electrodes to steer the electromagnetic field. Note that such a Gaussian pulse comprises a large number of different frequency components, each of which behaves differently in tissue. This alters the shape and propagation of the overall pulse. The centre frequency of the Gaussian pulses is generally in the GHz range, say from 1-50 GHz.

In one embodiment, the phased array system introduces a phase shift between adjacent electrodes. In general, the phased array system is controllable such that the phase shift can vary for any given electrode from zero up to some predetermined maximum, such as π/2 (N.B. the phase shift can have a positive or negative sign). In other embodiments, only the (constant) increment in phase shift between successive electrodes may be subject to external control.

One configuration of a phased array system comprises a linear, regularly spaced array with a constant increment in phase shift between successive array elements. This configuration then produces a planar wavefront whose angle to the array axis depends on the phase shift increment. Other embodiments may adopt a different configuration. For example, if the array elements have a regular spacing, but the phase shift increment varies between successive array elements, this may introduce curvature into the wavefront. In addition, the use of irregular spacing between the array elements may help to provide improved control of the wavefront at high frequencies in certain situations.

In more general terms, the phased array system may vary (a) spatially (in terms of the positioning of the different array elements); (b) temporally (in terms of the timing or phase applied to the different array elements); and (c) in terms of the signal amplitude and shape applied to the different array elements. It will be appreciated that (a) is normally determined by the design of the DBS apparatus and its position with the subject, but (b) and (c) can be controlled thereafter to help steer the electromagnetic field.

In one embodiment, at least some of the electronics for the phased array system in use are located with the electrodes in the skull of the user. This helps to avoid distortion or other degradation of pulse signals (e.g. distortion of the pulse shape or timing) as they travel from an IPG in the body to the electrode assembly in the head.

Another embodiment of the invention provides a method involving the use of the apparatus described above to perform deep brain stimulation. The electrode assembly of the apparatus can be implanted into the brain, and then various parameters associated with the phased array system can be adjusted by the clinician to optimise the patient response. For example, parameters that might be altered for this purpose include phase/timing delay between different electrodes, pulse duration and/or shape, which electrodes are activated (some may be completely turned off), signal form (e.g. single, repeated pulse, or sinusoidal waveform), single frequency, and so on.

BRIEF DESCRIPTION OF THE DRAWINGS

Various embodiments of the invention are now described in detail by way of example only with reference to the following drawings.

DETAILED DESCRIPTION

Figure 1:
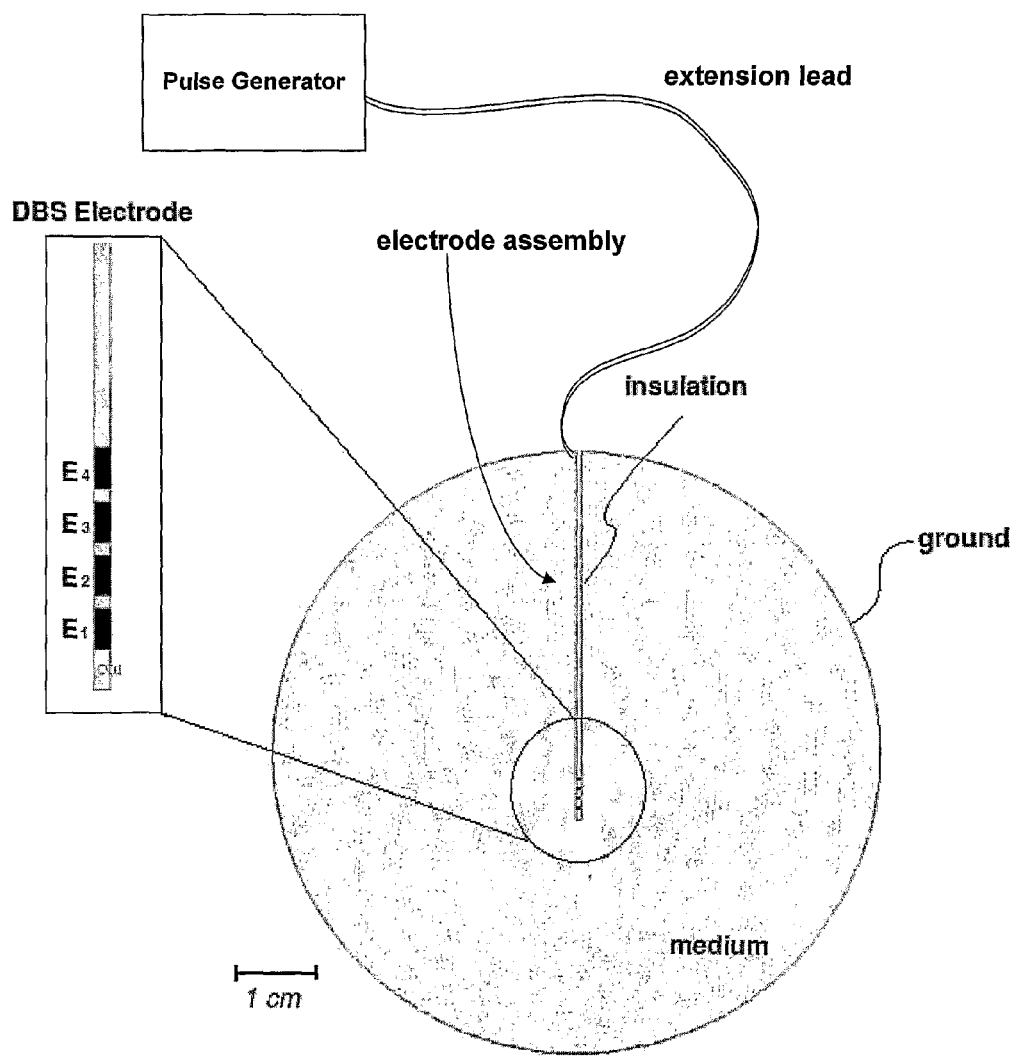
FIG. 1 is a schematic diagram illustrating apparatus involved in performing DBS.

The present approach is based on the use of a phased array (PA) in DBS to allow the control of the direction of the wavefront generated by the array. A PA includes an array multiple antenna elements. A variable phase or time-delay is then applied to each element to direct the radiated electric field from the PA in a desired angle.

The radiated electric field, $E(R_0,\theta,\phi)$, at a point $Q(R_0,\theta,\phi)$ of an antenna array having N elements is the sum of the contributions of the electric fields radiated from each element:

$$E(R_0, \vartheta, \phi) = f_e(\vartheta, \phi)\left(\frac{e^{-jkR_0}}{R_0}\right)\sum_{i=1}^{N}[A_1 e^{jikd\cos\vartheta}] \quad (1)$$

where $f_e(\theta,\phi)$ is the pattern generated by a single element, $e^{-jkR_0}/R_0$ represents the spherical propagation factor, $e^{jikd\cos\theta}$ indicates the phase of the propagation factor of each element, described by the wavenumber $k=2\pi/\lambda$, where $\lambda$ is the wavelength, and the distance, d, between elements, $A_i=a_i e^{j\beta_i}$ is the complex feeding coefficient, representing the amplitude, $a_i$, and phase, $\beta_i$, of the excitation of each individual element i, and $R_0$ denotes the distance from the far-field observation point Q to the array. In the far-field region the distance, $R_i$, between each element and the observation point is approximated to $R_0$, thus ignoring the distances from Q to each element.

Equation 1 (above) corresponds to the product of the field of a single element at a reference point and the array factor, AF, of the array:

$$AF = \sum_{i=1}^{N}[\alpha_i e^{j\beta_i}e^{jikd\cos\vartheta}] \quad (2)$$

The AF is governed by the array amplitude control, defined by the values of $a_i$, and the phase control, represented by the values of $\beta_i$. The amplitude distribution serves to control the shape of the array pattern, whereas the phase distribution is used to steer its direction. Beam steering can achieved by applying linearly incremental phase delays across the array. For example, the phase delay of the ith element relative to the zero-phase element may be expressed as $\beta_i=i\,\delta$, where $\delta$ is the incremental phase delay between adjacent elements. The AF can then be written as:

$$AF = \sum_{i=1}^{N}[\alpha_i e^{ji\delta}e^{jikd\cos\vartheta}] = \sum_{i=1}^{N}[\alpha_i e^{ji(kd\cos\vartheta-\delta)}] \quad (3)$$

where $\psi=kd\cos\theta+\delta$. The maximum radiation pattern can be shown to occur when $\psi=0$.

With this in mind, the behavior of the array pattern can be defined for different values of the incremental delay $\delta$. If $\delta$ is zero, the phase is uniform across the array and the maximum pattern occurs when $\psi=kd\cos\theta+\delta=kd\cos\theta=0$, hence at $\theta=90°$. This is known as broadside radiation.

On the other hand, if the maximum radiation is required at angle $\theta_0$, with $0°\leq\theta\leq180°$, the phase, $\beta$, needs to be adjusted so that:

$$\psi=kd\cos\theta+\delta|_{\theta=\theta_0}=kd\cos\theta_0+\delta=0\rightarrow\delta=-kd\cos\theta_0 \quad (4)$$

If the maximum pattern is required along the array axis (endfire), in either 0° or 180° directions, the incremental delay needs to be chosen such that $$\psi=kd\cos\theta+\delta|_{\theta=0°}=kd+\delta=0 \quad (5)$$

thus $\delta=-kd$.

In practice, when a pulse is fed to one of the array elements, it generates a wavefront which propagates in the given medium. The wavefronts from each element add constructively and destructively resulting in the generation of an overall wavefront. This wavefront travels at a velocity, $v_p$, in the medium. By applying a time delay, $t_d$, or a phase delay, $\beta_i$, between the excitation of adjacent elements, the wavefront generated by one pulse travels a distance $v_p/t$, before the next element of the array is excited, resulting in the wavefronts merging at a specific angle with respect to the perpendicular to the array axis. By controlling the time delay between the excitation of the elements of the phased array, the direction of the beam can be likewise controlled.

The angle between the main beam and the perpendicular to the array axis is defined in terms of time delay as:

$$\theta_0 = \cos^{-1}\left(\frac{v_p t_d}{d}\right) \quad (6)$$

and in terms of phase delay as:

$$\theta_0 = \cos^{-1}\left(\frac{\beta}{kd}\right) \quad (7)$$

The beam steering angle is therefore dependent of the velocity of the medium and the distance between the elements.

Figure 2:
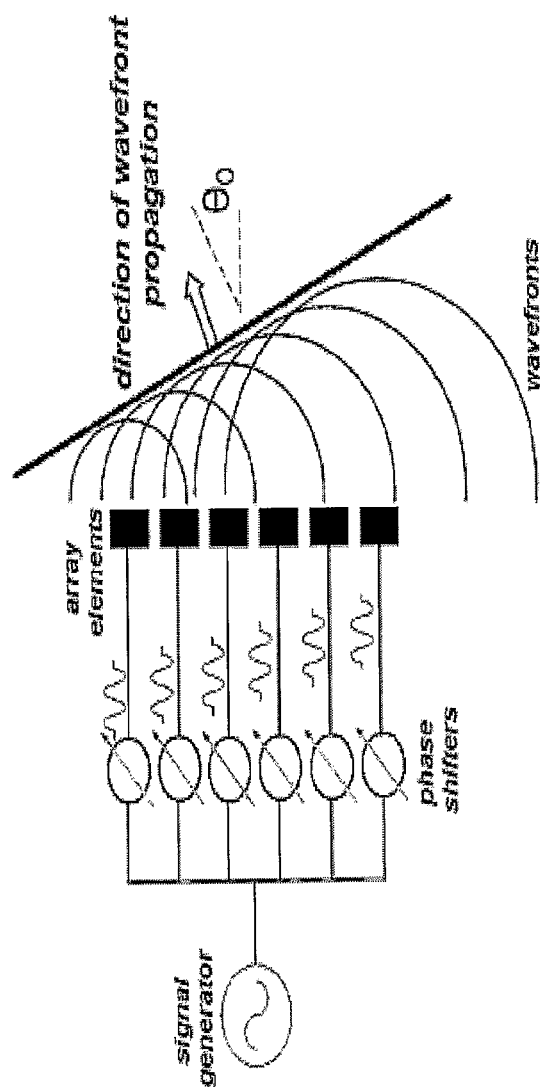
FIG. 2 is a schematic diagram of a linear phased array (PA) system.

FIG. 2 illustrates in schematic form a PA comprising a set of array elements. A common signal is sent to the array elements, which is then subjected to a controlled delay as described above prior to emission. This in turn alters the angle of the wavefront, $\theta$, as shown in FIG. 2. (N.B. the angle $\theta$ as marked in FIG. 2 is measured with respect to the broadside propagation direction, not the linear array axis as for Equations 6 and 7 above). In particular, if all the elements have a common delay in FIG. 2, $\theta=0$, such that the wavefront propagates in a direction perpendicular to the array axis. However, an appropriate choice of delays for the elements can alter the direction of the wavefront away from the perpendicular to give non-zero values for $\theta=0$, such as shown in FIG. 2. More generally, the beam angle is dependent on the applied delay, the medium properties, and the geometry of the array.

Note that the PA in FIG. 2 comprises a linear array, in that all the array elements are located on a single line. In this configuration, the wavefront is circularly symmetric about the linear axis of the array (and therefore would be conical in shape), assuming a homogeneous and isotropic medium. It is also possible to have two (or three) dimensional arrays to provide additional control of the wavefront.

The DBS system of FIG. 1 can be utilised as a PA system by making the different electrodes of the electrode assembly represent the array elements. Simulation of this system was performed by using a 2D finite element representation (using the Comsol package from Sweden, see www.comsol.com) of a 3389 Medtronic DBS electrode.

The dielectric properties of brain tissues are frequency-dependent and highly non-linear. The dielectric spectrum can be divided into three main regions, which describe low, medium and high frequency dielectric behaviour. Each of these regions is characterized by a polarization mechanism governed by the Debye relation:

$$\varepsilon_c(\omega) = \varepsilon_\infty + \frac{\varepsilon_s - \varepsilon_\infty}{1 + j\omega\tau} \tag{8}$$

where $\varepsilon_\infty$ is the permittivity at high frequencies (as $\omega \to \infty$), $\varepsilon_s$ is the permittivity at DC and $\tau$ is the relaxation time constant. In order to account simultaneously for the dispersions related to each frequency relation, a distribution parameter $\alpha$ can be added to the Debye equation:

$$\varepsilon_c(\omega) = \varepsilon_\infty + \frac{\varepsilon_s - \varepsilon_\infty}{1 + (j\omega\tau)^{1-\alpha}} \tag{9}$$

To model the dielectric spectrum of different types of tissues, multiple Cole-Cole dispersion relations can be used, resulting in:

$$\varepsilon_c(\omega) = \varepsilon_\infty + \sum_{n=1}^{4} \frac{\Delta\varepsilon_n}{1 + (j\omega\tau_n)^{1-\alpha_n}} + \frac{\sigma_i}{j\omega\varepsilon_0} \tag{10}$$

where $\sigma_i$ is the ionic static conductivity and $\varepsilon_0$ is the permittivity of free space (see Gabriel et al., "The dielectric properties of biological tissues: Iii. parametric models for the dielectric spectrum of tissues", *Phys med Biol*, vol. 41, no. 11, pp. 2271-2293, November 1996). The modeling described herein adopts the tissue permittivity specified by Equation 10. Typical values to represent the dielectric properties of the grey matter for a homogeneous tissue and for DBS frequencies are conductivity $\sigma=0.098$ S/m and permittivity $\varepsilon=2463000$ F/m.

Note that for the GHz frequencies utilised herein, the resulting field is modeled as an electromagnetic field whose propagation depends on both the electrical and magnetic properties of the brain. However, it is possible that the physiological or neurological impact of the stimulation may arise from the resulting electric field component.

The 3389 Medtronic DBS electrode has four electrodes, each 1.27 mm in diameter, 1.5 mm long, and separated from one another by 0.5 mm. This gives a total separation between array elements of 2 mm (corresponding to the value of d in Equations 6 and 7 above). This source was assumed to be placed at the centre of a homogeneous, isotropic medium, represented as a circular mesh of radius 50 mm (such as shown in FIG. 1). Note that for ease of computation, the electrode contacts were treated as point sources. In addition, a more sophisticated model would introduce space-dependent conductivity and permittivity to represent different anatomical regions of the brain. Neumann conditions were imposed on the electrode insulating shaft and spacings between the electrode contacts and Dirichlet conditions were set on the medium outer boundary, to represent the system's reference.

The brain behaves as a lossy dielectric (or poor conductor), therefore acting on electromagnetic waves by imposing attenuation during their propagation. If we assume brain tissue to behave as an isotropic, homogeneous medium, then the propagation of time-harmonic waves is governed by the Helmholtz equation:

$$\nabla^2 \tilde{E}_s - \gamma^2 \tilde{E}_s = 0 \tag{11}$$

where $E_s$ represents the time harmonic wave in phasor form and $\gamma$ is a complex quantity representing the propagation constant of the medium given by:

$$\gamma^2 = j\omega\mu(\sigma + j\omega\varepsilon) \tag{12}$$

If we define $\gamma$ as $\gamma = \alpha + j\beta$, where $\alpha$ and $\beta$ represent the attenuation and phase constant of the medium respectively, and are defined as:

$$\alpha = \omega\sqrt{\frac{\mu\varepsilon}{2}\left[\sqrt{1 + \left[\frac{\sigma}{\omega\varepsilon}\right]^2} - 1\right]} \tag{13}$$

$$\beta = \omega\sqrt{\frac{\mu\varepsilon}{2}\left[\sqrt{1 + \left[\frac{\sigma}{\omega\varepsilon}\right]^2} + 1\right]}$$

This modelling can help with the understanding of DBS mechanisms, leading to improved designs for electrodes and overall DBS systems that provide better steering and focussing of the electric field. This permits better control of the direction, shape and intensity of the electric field within the brain, which in turn can help to enhance clinical benefit and to reduce DBS side effects.

Figure 3:
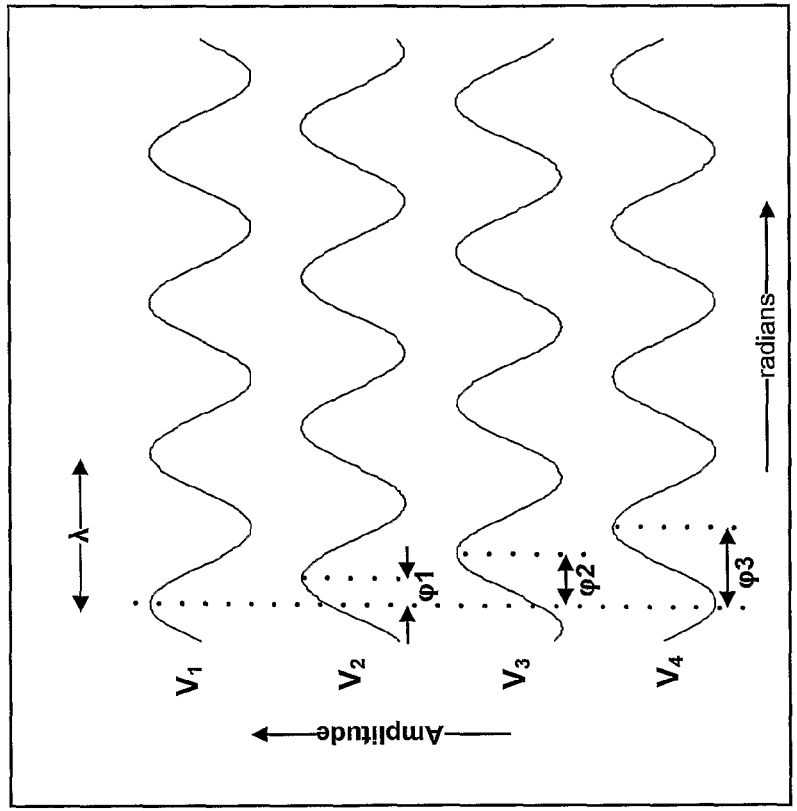
FIG. 3 illustrates the sinusoidal signals used in the models of FIG. 4.

In one experiment, the stimulation signal is sinusoidal, as shown in FIG. 3, although it was then subject to supply in pulsed form, as for conventional DBS. In other words, each pulse of approximately 60-120 µs comprises a sinusoidal wave (of frequency in the GHz region), and there is a pulse repetition rate of approximately 130-185 Hz. The GHz frequency has been found to provide a good trade-off between field steering, focussing and tissue penetration. The amplitude of the sinusoidal waveform is 2V, and there is a constant offset in phase between successive electrodes. The model assumes wavelengths less than 1 mm, which permits the wavefront to be controlled within the DBS target region, which has a radius of approximately 10 mm.

Figure 4:
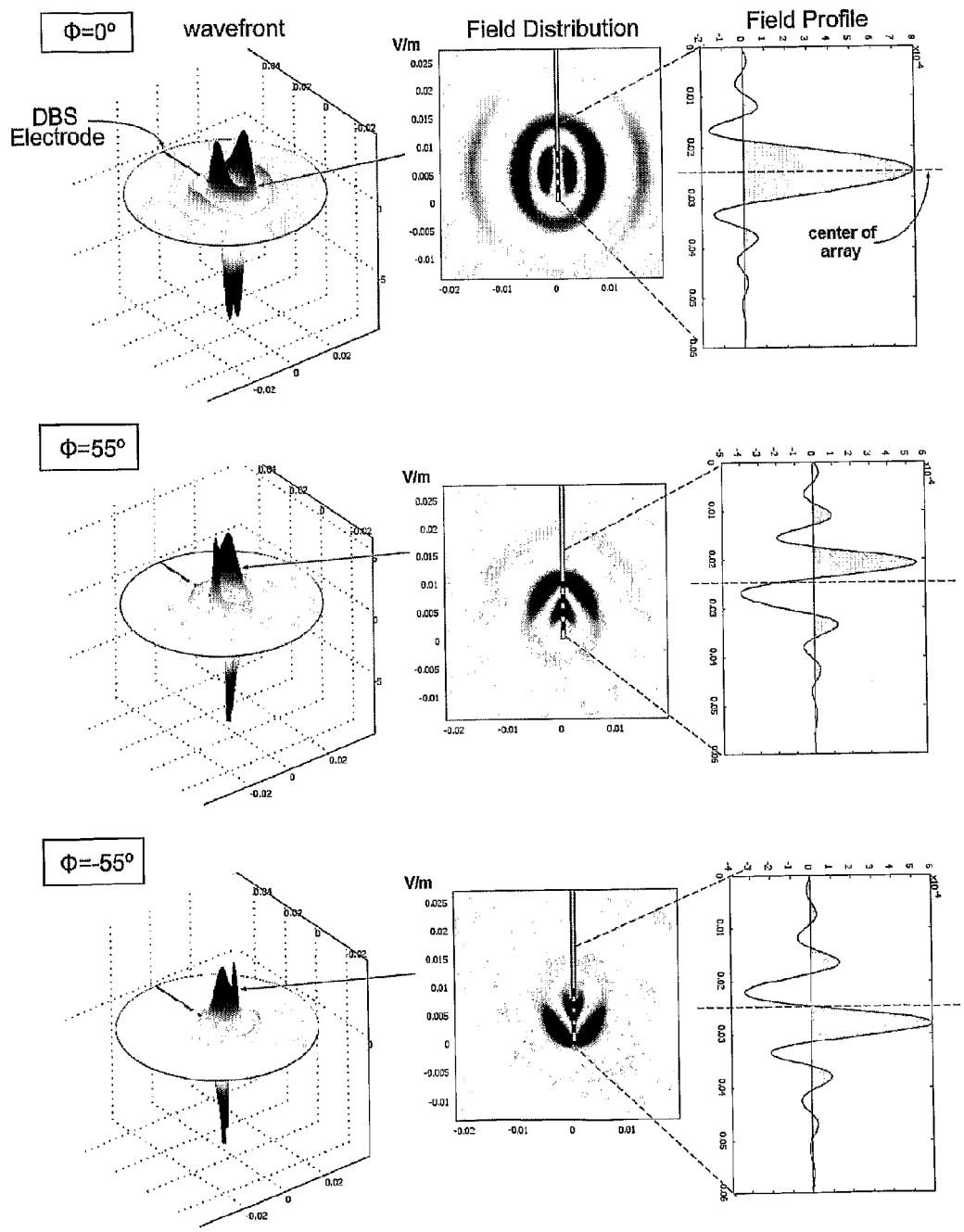
FIG. 4 depicts modeled wavefront propagation in accordance with one embodiment of the invention.

The wave equation was solved for values of phase shifts between $-\pi/2$ and $+\pi/2$ and for frequencies in the range 1-10 GHz. The minimum frequency of operation was set at 1 GHz since this corresponds to wavelengths of approximately 40 mm in tissue (and hence within the FEM model area). The angle of wave propagation, $\theta_0$, was estimated as per equations 6 and 7. FIG. 4 illustrates the 2-D modeled wavefront propagation for this experiment with a frequency of 5 GHz. The left-hand plots show a 3-D view of the location and angles of propagation of the wavefronts with respect to the array axis; the middle plots show a detailed view of the distribution of the electric field in the proximity of the source; and the right-hand plots represent profiles of the field distributions along the array axis. As the phase shift is varied, the location of the stimulating field (shaded area) is steered to the left or right with respect to the centre of the array. At phase-shift 0 we have broadside propagation, but the direction of radiation alters as an increasing (absolute) phase-shift is introduced, until end-fire propagation is achieved at a phase shift of $\pm\pi/2$.

Figure 5:
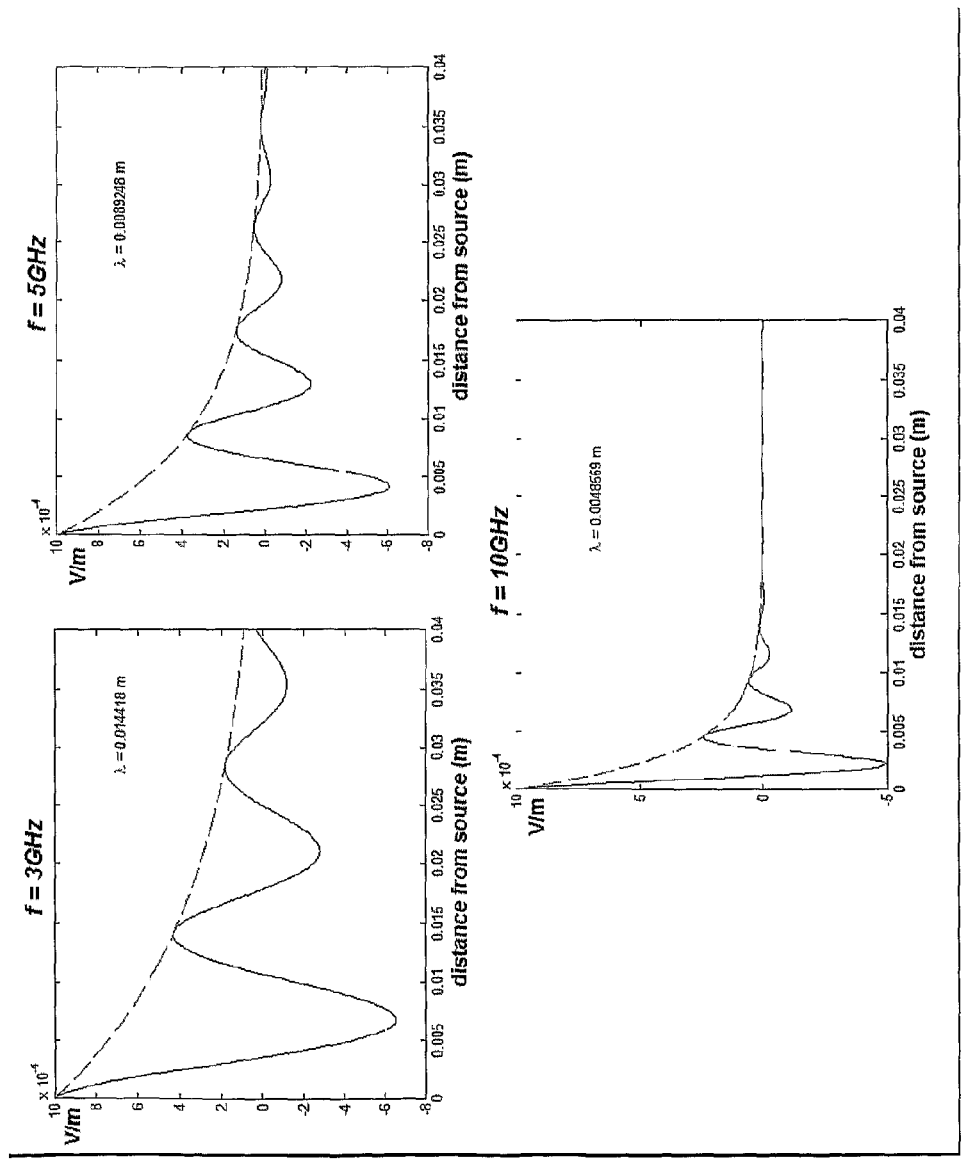
FIG. 5 depicts modeled wavefront attenuation in accordance with one embodiment of the invention.

In all cases the waves are attenuated by the medium properties. The depth of penetration of the propagating wave is inversely proportional to the frequency of operation, as shown in FIG. 5 for frequencies of 3 GHz, 5 GHz and 10 GHz. The solid lines in FIG. 5 represent the amplitude of the propagating waves, while the dashed line represents the attenuation factor described by $e^{-\alpha x}$, where x is the distance from the source. The depth of penetration was determined as the distance from the source where the amplitude of the wave falls to $e^{-1}$, or about 37% of its maximum value. This occurs at a distance from the array of 16 mm at 3 GHz, 8.8 mm at 5 GHz, and 3.3 mm at 10 GHz.

Figure 6:
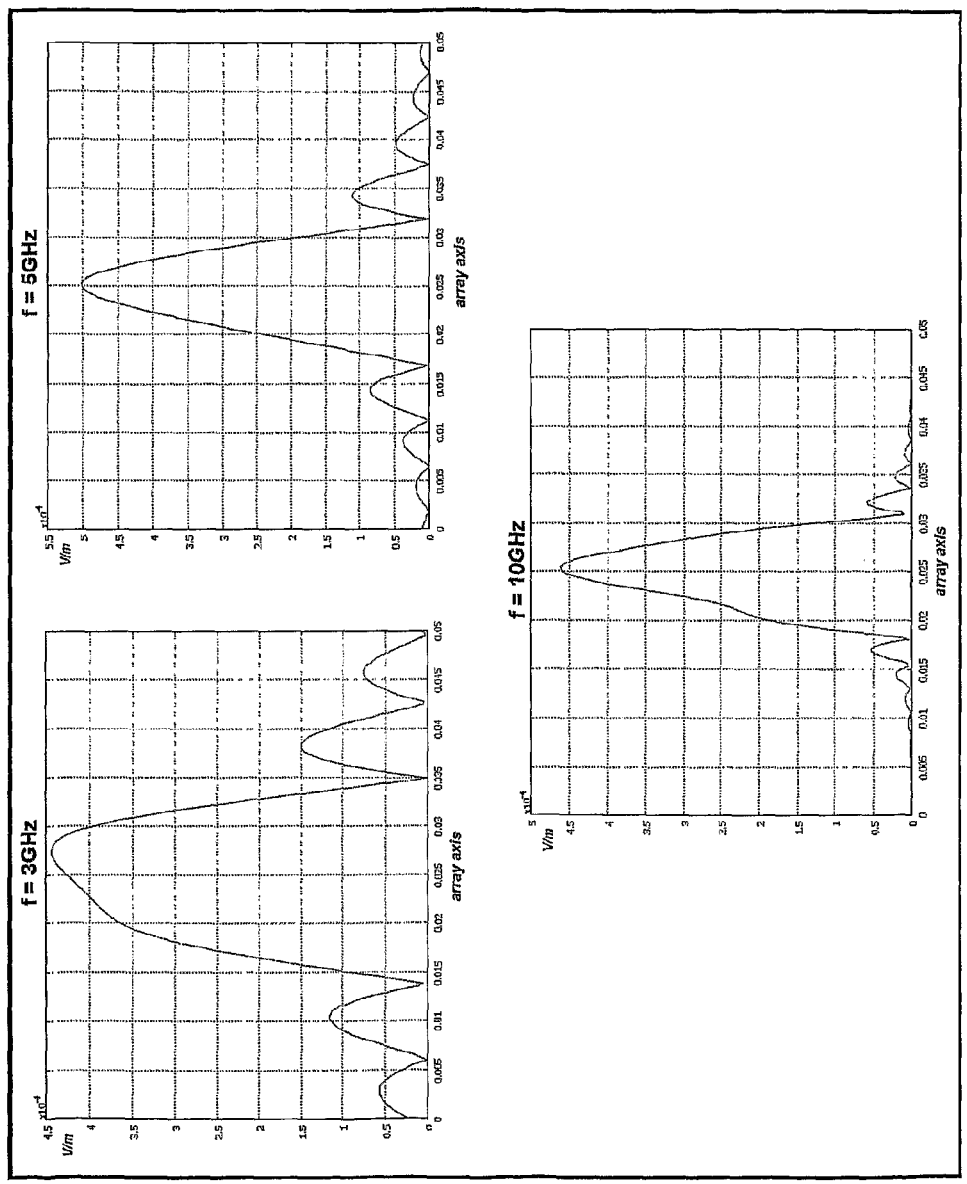
FIG. 6 depicts wavefront profiles in accordance with one embodiment of the invention.

The size of the traveling wavefront, i.e. the area of stimulation, is also dependent on the frequency of operation. FIG. 6 illustrates the profiles of the wavefronts generated by the phased array source at 3 Ghz, 5 GHz and 10 GHz, with no phase shift applied. The measured widths of the wavefronts were approximately 22 mm at 3 GHz, 16 mm at 5 GHz, and reducing to about 12 mm at 10 GHz.

FIG. 4-6 illustrate the ability to control the direction of wavefront propagation by varying the incremental phase shift between the excitation of the array elements. In addition, the frequency of operation can be used as a control parameter to define the area (focus) and depth of penetration of the stimulating field. This ability to steer and focus the field is a major improvement on conventional DBS system which are characterized by poor stimulation selectivity. The present approach should therefore allow a reduction in side effects resulting from the stimulation of non-target areas, as well as providing a facility for more selective and focused stimulation of different areas of the brain, thereby contributing to the understanding of brain operation.

Although the experiments of FIGS. 4-6 utilised sinusoidal signals with frequencies in the range 1-10 GHz, other signals could be used instead. For example, higher frequencies of up to say 50 GHz might be used (or possibly even higher into the TeraHz range). In addition, pulsed signals (such as Gaussian pulsed signals) might be used instead of a sinusoidal wave, with the timing of the pulses staggered between the various electrodes to steer the electric field.

Figure 7:
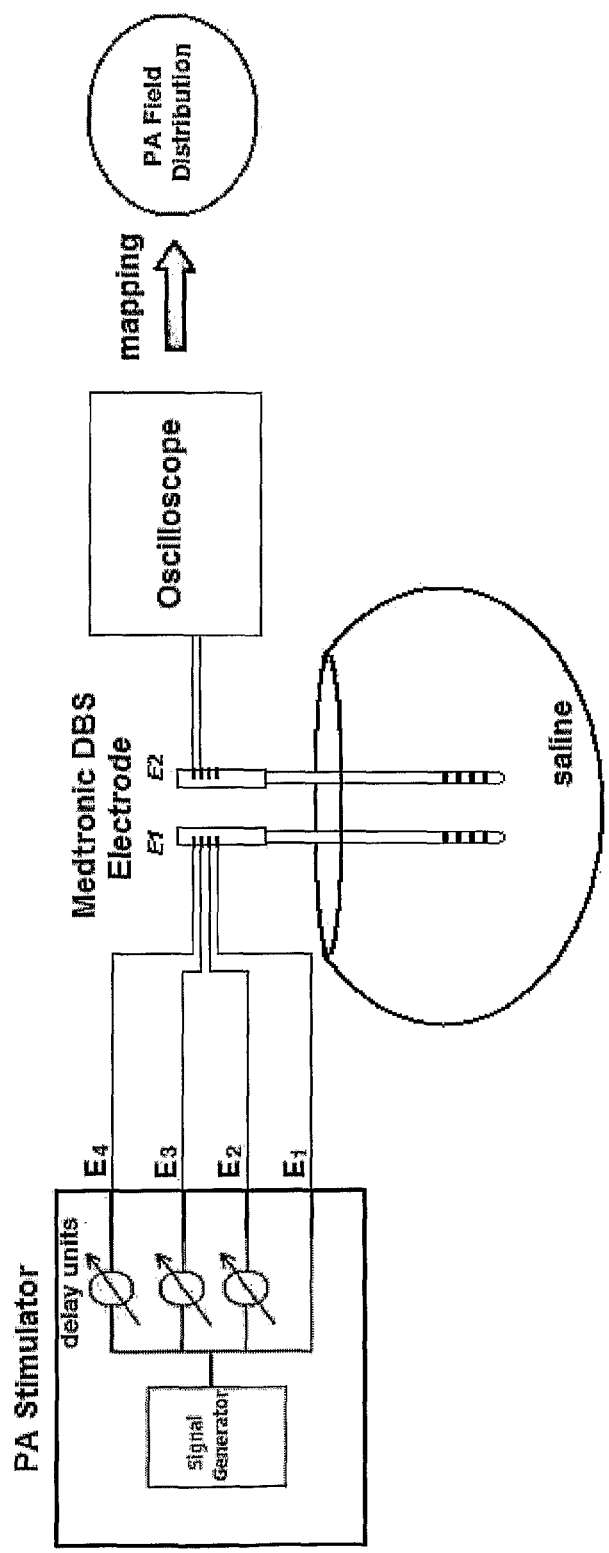
FIG. 7 illustrates laboratory testing of the DBS apparatus in accordance with one embodiment of the invention.

FIG. 7 illustrates apparatus for further testing of the approach described herein. In this case rather than having a computer model, a physical DBS system is used to drive a real electrode assembly which is located in a saline medium to represent the brain. A second electrode assembly is located in the saline to measure the electric field generated by the first electrode assembly. It will be appreciated that the positioning of this second electrode assembly may be varied to measure the field strength in different locations and orientations with respect to the first electrode assembly.

Figure 8:
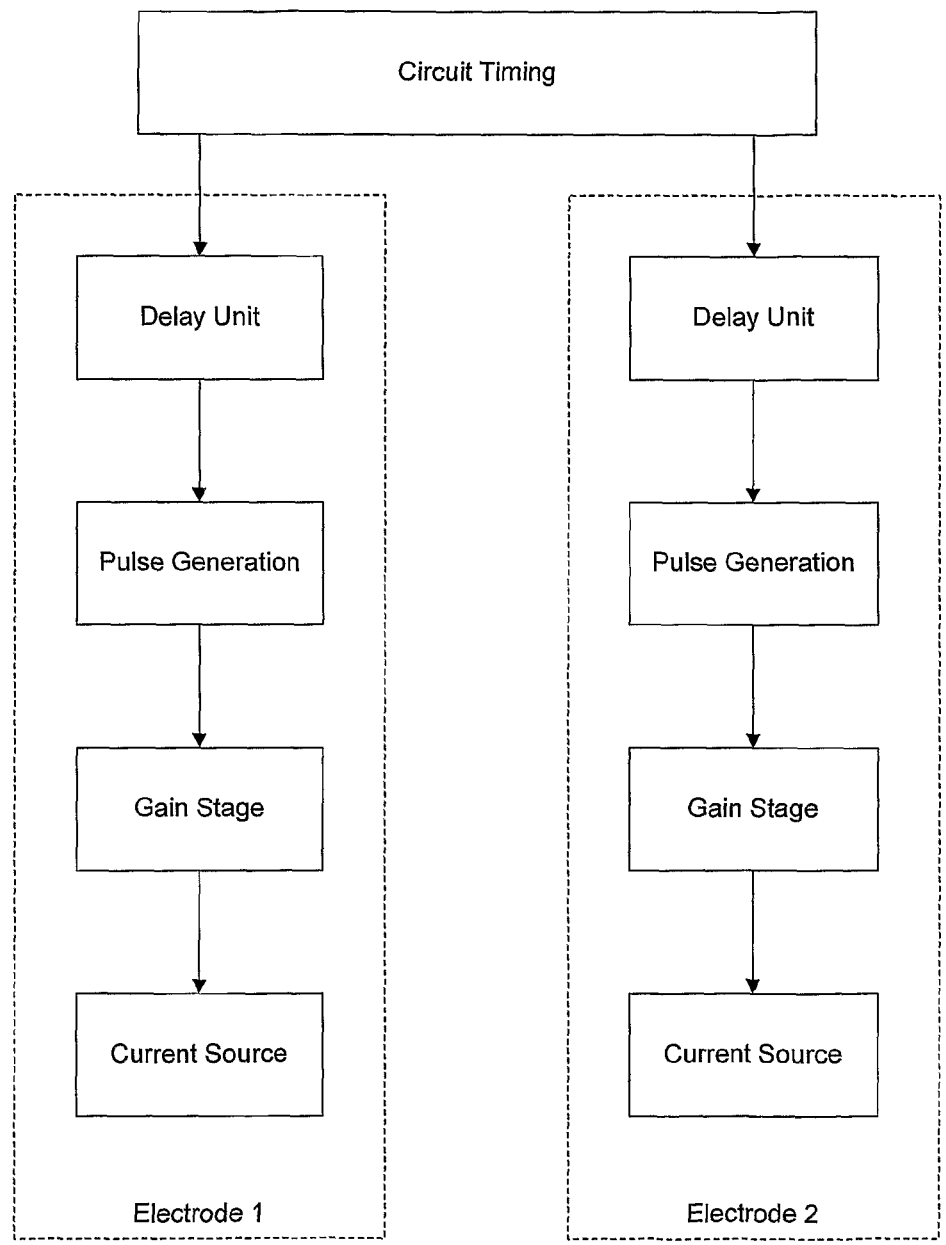
FIG. 8 is a schematic diagram of control electronics for the DBS apparatus in accordance with one embodiment of the invention.

FIG. 8 is a schematic diagram showing the electronic control portion of the phased array system. FIG. 8 shows electronics for controlling two electrodes, but the system can be readily extended to support additional electrodes by replicating the units depicted within the dashed boxes (one dashed box per electrode).

As shown in FIG. 8, signal generation is controlled and initiated by a circuit timing unit, which transmits trigger signals to the various electrodes. The timing of this trigger signal is the same for all electrodes. Each electrode then has an associated delay unit, which delays the trigger signal by the appropriate amount for that electrode according to the phased array structure. In general, the amount of delay applied to each electrode can be adjusted to control steering of the electromagnetic field. The delayed trigger signal is passed to a pulse generator, which generates a pulse of the appropriate shape. The signal from the pulse generator is then amplified through a gain stage, before being driven onto the array electrode by a current source.

It will be appreciated that the electronic configuration of FIG. 8 is by way of example only, and other circuit arrangements are possible. For example, the circuit timing unit may itself generate an initial pulse, which is then passed through the delay stages before being applied to the electronics. In addition, different components may be utilised to generate the stimulation signal, such as some form of oscillator to produce a harmonic (e.g. sinusoidal) output, such as illustrated in FIG. 3.

The location of the control electronics shown in FIG. 8 may also be adapted according to particular requirements. As discussed in relation to FIG. 1, a conventional IPG is normally located within the torso, remote from the electrode assembly itself. However, in certain embodiments, some or all of the electronics shown in FIG. 8 may be located inside the skull with the electrode assembly. This reduces sensitivity to noise induced in the leads, as well as reducing timing jitter and/or signal distortion resulting from the propagation along the leads between the pulse generator(s) and the electrode assembly. This type of noise suppression is attractive for a phased array system, given the use of shorter pulses and/or higher frequencies than for conventional DBS systems, plus the importance of pulse timing and shape. In some implementations, the system may include the facility to re-shape pulses close to the electrode assembly in order to overcome any distortions introduced into the leads during propagation from the IPG.

Although various embodiments have been discussed by way of example, the skilled person will be aware of many further modifications to these embodiments without departing from the scope of the invention as defined by the appended claims and their equivalents.

What is claimed is:

1. An apparatus for performing deep brain stimulation with an electromagnetic field, the apparatus including an electrode assembly having multiple electrodes and a phased array system for driving the electrodes to generate the electromagnetic field, wherein the phased array system generates a high frequency sinusoidal signal for supply to the multiple electrodes, wherein the phase of the signal is staggered between different electrodes to steer the electromagnetic field.

2. The apparatus of claim 1, wherein the multiple electrodes comprise a linear array of electrodes.

3. The apparatus of claim 1, wherein the multiple electrodes comprise 8 or more electrodes.

4. The apparatus of claim 1, wherein the sinusoidal signal has a frequency of 1 GHz or more.

5. The apparatus of claim 4, wherein the sinusoidal signal has a frequency of 50 GHz or less.

6. The apparatus of claim 5, wherein the sinusoidal signal has a wavelength in the brain comparable with the volume of tissue to be activated.

7. The apparatus of claim 5, wherein a periodic on-off duty cycle is imposed onto the sinusoidal signal.

8. The apparatus of claim 7, wherein said duty cycle has a frequency in the range 100-200 Hz.

9. The apparatus of claim 7, wherein the on portion of the duty cycle has a period in the range 1-100 μs.

10. The apparatus of claim 1, wherein the phased array system is controllable such that the phased array system can vary the phase shift between adjacent electrodes from zero up to a predetermined maximum.

11. The apparatus of claim 10, wherein said predetermined maximum is π/2.

12. The apparatus of claim 1, wherein the phased array system includes a delay element for each electrode.

13. The apparatus of claim 1, wherein electronics for the phased array system in use are adapted for location at least partly with the electrodes in the skull of the subject.

* * * * *